United States Patent

Müller et al.

[11] Patent Number: 5,412,827
[45] Date of Patent: May 9, 1995

[54] TOOTHBRUSH

[75] Inventors: Ingo Müller, Klagenfurt; Norbert Schneider, Ebental, Austria; Erich Krammer, Klagenfurt, all of

[73] Assignee: U.S. Philips Corporation, New York, N.Y.

[21] Appl. No.: 280,915

[22] Filed: Jul. 27, 1994

[30] Foreign Application Priority Data

Jul. 30, 1993 [BE] Belgium .............................. 09300795

[51] Int. Cl.6 ...................... A61C 17/34; A46B 13/02; A46B 7/06
[52] U.S. Cl. ..................................... 15/22.1; 15/167.1; 15/172
[58] Field of Search ....................... 15/22.1, 22.1, 22.4, 15/167.1, 167.2, 172

[56] References Cited

U.S. PATENT DOCUMENTS 3,859,684 1/1975 Moskwinski .............................. 15/23

FOREIGN PATENT DOCUMENTS 0481553 4/1992 European Pat. Off. ............. 15/22.1
2002159 2/1992 WIPO .................................... 15/22.1
2010979 7/1992 WIPO .................................... 15/22.1

Primary Examiner—Edward L. Roberts, Jr.
Attorney, Agent, or Firm—Ernestine C. Bartlett

[57] ABSTRACT

A toothbrush is provided having two housing sections (1, 2) which are pivotable relative to one another, of which a first housing section (1) serves as a handle and accommodates a drive unit (4) for driving a drive shaft (5), and of which a second housing section (2) carries a brush-head (3), which is drivable by the drive shaft, which second housing section (2) is pivotable relative to the drive shaft (5) about a pivot (6). To warn the user against an excessive brushing pressure the toothbrush has a spring device with at least one spring (14) which acts between the second housing section (2) and the drive shaft (5), the second housing section (2) being pivotable relative to the first housing section (1) about the pivot (6) against a pressure exerted by the spring (14) during use of the toothbrush, which spring snaps when a given pressure threshold is exceeded and which pivot is disposed in the second housing section and also forms at least a part of a mechanical coupling between the drive shaft and the second housing section.

7 Claims, 3 Drawing Sheets

TOOTHBRUSH

FIELD OF THE INVENTION

The invention relates to a toothbrush having two housing sections which are pivotable relative to one another, of which a first housing section serves as a handle and accommodates a drive unit for driving a drive shaft, and of which a second housing section carries a brush-head, which is drivable by the drive shaft, which second housing section is pivotable relative to the drive shaft about a pivot.

BACKGROUND OF THE INVENTION

Such a toothbrush is known from U.S. Pat. No. 3,859,684.

This known toothbrush comprises a rotatable brush having a brush shaft pivotably connected to a drive shaft by means of a universal joint, the drive shaft being situated in a first housing section. The brush shaft is enclosed by a second housing section, which projects into the first housing section. A switching spring is arranged between the housing sections to turn on the motor when the second housing section is pivoted relative to the first housing section during use.

The force with which the brush is pushed against the teeth is important for a proper cleaning action. To remove dental plaque a certain pressure must be applied. However, the brushing pressure should not be too high because the brush also comes into contact with, for example, the gums and the tooth necks during brushing. The tooth brush in accordance with U.S. Pat. No. 3,859,684 does not provide such protection.

SUMMARY OF THE INVENTION

It is an object of the invention to provide a toothbrush of simple construction including a safety feature to warn the user when the brushing pressure is too high.

To this end the invention is characterized in that the toothbrush comprises a spring device having at least one spring which acts between the second housing section and the drive shaft, the second housing section being pivotable relative to the first housing section about the pivot against a pressure exerted by the spring during use of the toothbrush, which spring snaps when a given pressure threshold is exceeded and which pivot is disposed in the second housing section and also forms at least a part of a mechanical coupling between the drive shaft and the second housing section.

Snapping is to be understood to mean a suddenly occurring acceleration or deceleration. The snapping effect warns the user of too high a brushing pressure.

Another advantage of the toothbrush, apart from the overpressure warning, is that by arranging the pivot in the second housing section the sealing for the passage of the drive shaft through a wall of the first housing section can be simple and reliable because at the location of the wall the drive shaft does not perform a pivotal movement but almost exclusively a translational or rotational movement.

It is to be noted that toothbrushes are known comprising two pivotable housing sections and a spring device whose spring acts between the housing sections and in which during use of the toothbrush the second housing section is also pivotable relative to the first housing section about a pivot against a pressure exerted by the spring, which spring snaps when a certain pressure threshold is exceeded. However, in these toothbrushes the pivot is integrated in the first housing section in the drive mechanism, which leads to an expensive and intricate construction.

A preferred embodiment of the toothbrush is characterized in that the second housing section is provided with a coupling member as a part of said mechanical coupling, which coupling member is pivotable about the pivot, and the second housing section is detachably coupled to the drive shaft by means of the coupling member. This makes it possible for the user to replace a worn brush by a new comparatively cheap housing section with brush-head. The user also has the possibility of, for example temporarily, changing the brushing pressure by using another housing section with a brush-head whose spring device comprises a spring of greater or, conversely, smaller stiffness.

Another preferred embodiment of the toothbrush is characterized in that the spring device comprises a plate arranged in the second housing section, which plate has an opening through which the drive shaft extends and which plate has resilient arms, which are in resilient engagement with the drive shaft, and a stop, against which the drive shaft abuts after snapping. This provides a very simple, cheap and efficient construction.

Yet another preferred embodiment of the toothbrush is characterized in that there is provided a second spring having one end fixedly connected to the coupling member and having another end which snaps past a projection of the second housing section when the pressure threshold is reached. The snapping effect, which is attended with a clicking sound, is obtained by means of a cheap separate spring, which can be a plastics part which is integral with, for example, the coupling member.

Preferably, the second housing section resumes its original position when the pressure decreases after the threshold has been exceeded.

In a further embodiment of the toothbrush the plate is detachably mounted in the second housing section. This makes it possible to simply replace a plate providing a given pressure threshold by another plate providing a different threshold.

BRIEF DESCRIPTION OF THE DRAWINGS

An embodiment of the invention will now be described in more detail, by way of example, with reference to the drawings. In the drawings.

DETAILED DESCRIPTION OF THE PREFERRED EMBODIMENTS

Figure 1:
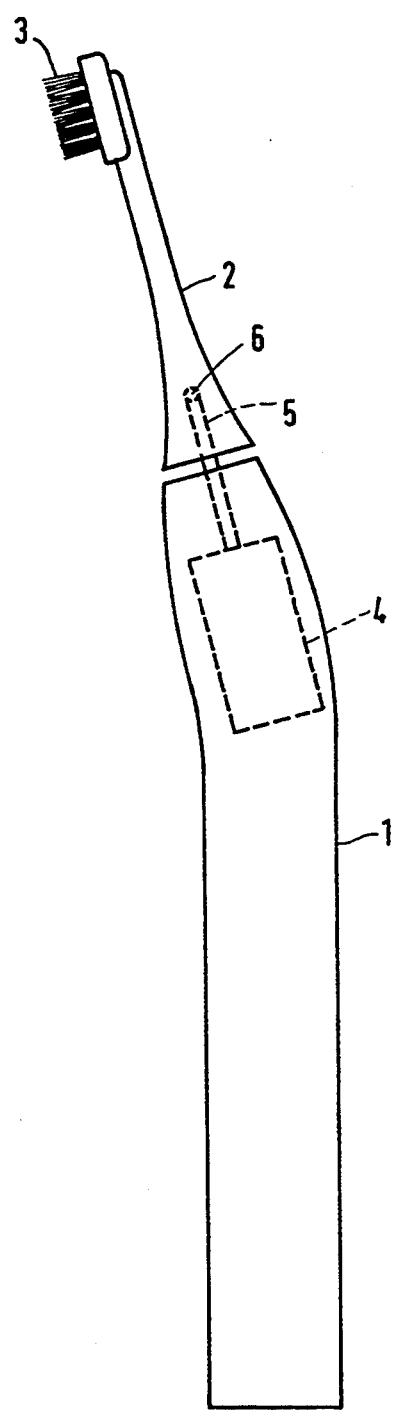
FIG. 1 is a side view of a toothbrush.

The toothbrush in accordance with the invention has two housing sections 1 and 2 which are pivotable relative to one another. The first housing section 1 serves as a handle and the second housing section 2 carries a brush-head 3, which may be integral with the second housing section or which may be detachably connected to the second housing section. The first housing section 1 accommodates a drive unit 4 for driving a drive shaft 5. The housing section 2 is pivotably connected to the drive shaft 5 by means of a pivot 6.

As is shown in FIGS. 2 through 5, the end portion 7 of the drive shaft 5 carries a coupling member 8. This coupling member is supported in the second housing section 2 so as to be pivotable about the pivot 6. For this purpose the coupling member has trunnions 9 which are engageable in corresponding openings 10 in the wall of the second housing section 2. The coupling member 8 couples the second housing section to the drive shaft 5. Preferably, this coupling is detachable. The second housing section has an open end 11 at its side which faces the first housing section 1. In this open end a plate 12 is fitted which has an opening 13 through which the drive shaft 5 extends. The plate 12 has two resilient arms 14. The drive shaft 5 is in resilient engagement with these resilient arms 14. The plate 12 further carries a stop 15 for the drive shaft (see also FIG. 5).

Figure 2:
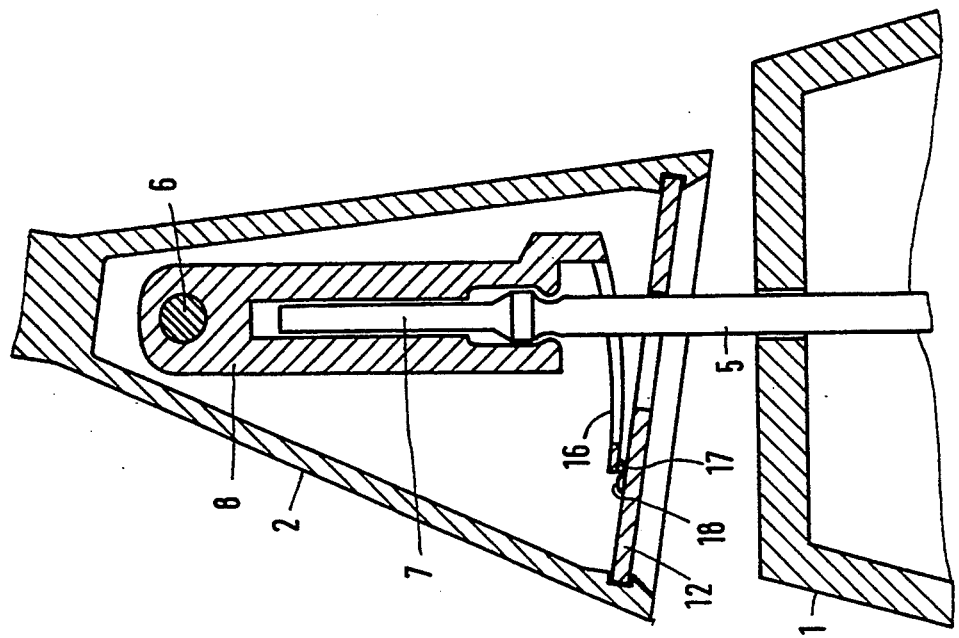
FIG. 2 is a partly sectional view showing the toothbrush of FIG. 1 in a situation in which no brushing is effected.
Figure 3:
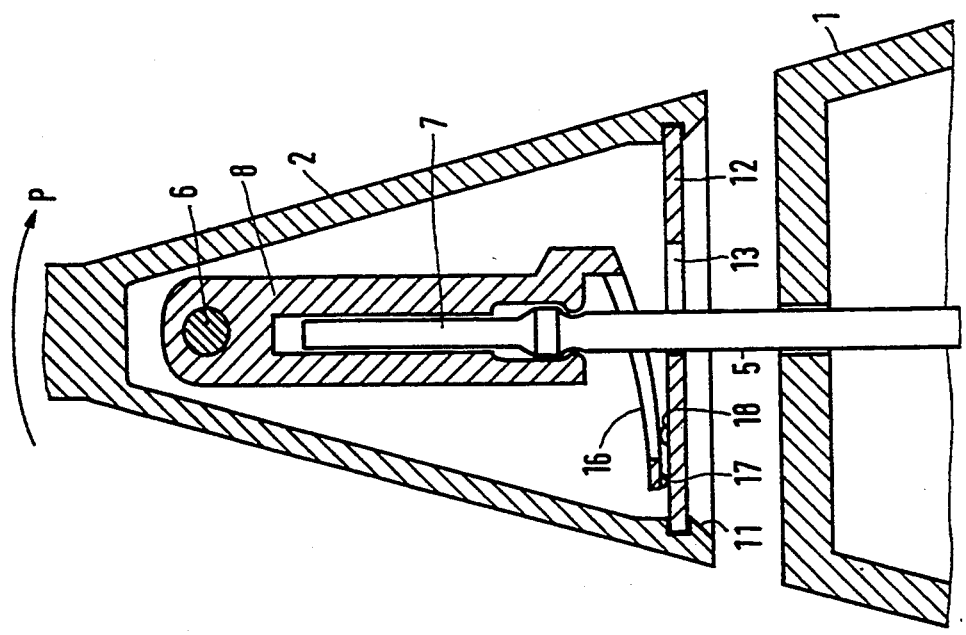
FIG. 3 is a partly sectional view of the toothbrush similar to FIG. 2 but in a pivoted position of the second housing section when the pressure threshold has been exceeded.
Figure 4:
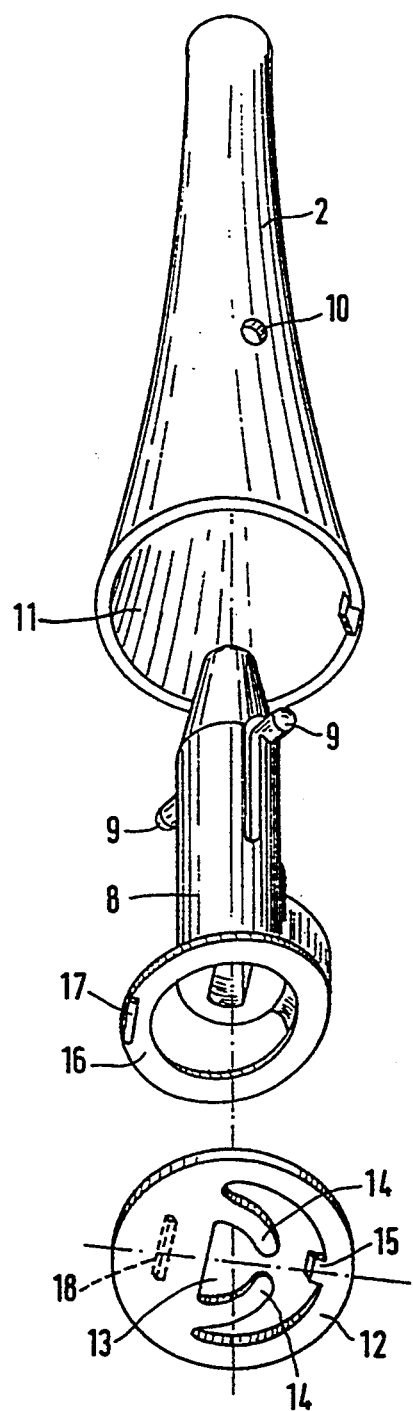
FIG. 4 is an exploded view of the second housing section with the coupling member and the plate.
Figure 5:
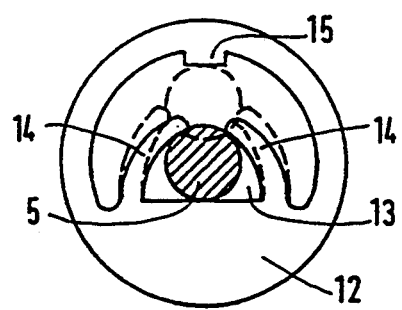
FIG. 5 shows the plate with the resilient arms and the drive shaft.

FIG. 2 shows the toothbrush in a situation in which no brushing is effected and no force is exerted on the brush-head 3. The resilient arms 14 preload the drive shaft 5, thereby holding the housing section 2 with the brush-head in the position shown in FIG. 2. During brushing the second housing section 2 is subjected to a force which urges the second housing section in a clockwise direction P. The drive shaft 5 pushes the resilient arms 14 outward. When a given pressure threshold is exceeded the drive shaft 5 snaps out of the resilient arms 14 and abuts against the stop 15 (FIGS. 3 and 5). This snapping is attended with an abrupt movement of the second housing section carrying the brush-head and thereby signals the user that the brushing pressure is too high. Subsequently, the user can reset the second housing section by hand into the position as shown in FIG. 2.

Alternatively, the resilient arms 14 may be given such a shape that the drive shaft 5 (or the resilient arms) does not snap but only an increasing spring force of the resilient arms is experienced upon a further pivotal movement. To warn the user nonetheless against an excessive pressure the coupling member 8 is provided with a second spring 16. This annular second spring is secured to the coupling member 8 or may be integral with the coupling member. The spring 16 has a nose 17 which engages resiliently against the surface of the plate 12. The surface of the plate carries a projection 18 for cooperation with the nose 17 of the spring 16. At the instant at which the pressure becomes too high the nose 17 of the second spring snaps past the projection 18, thereby signalling the user that the pressure is too high. When the pressure applied to the teeth decreases the nose of the second spring moves back over the projection. Thus, the user can normally continue brushing and will be warned again the next time that an excessive pressure occurs. Obviously, the nose 17 of the spring 16 may also engage against a projection on a wall of the housing section 2.

The plate 12 may be mounted detachably in the second housing section. This enables the use of plates having resilient arms of different stiffnesses, which consequently provide different pressure thresholds. For example, a plate providing a threshold value between 1.5 and 2.5N may be used for children or adults with sensitive gums and between 2.5 and 3.5N for adults with normal gums.

We claim:

1. A toothbrush having two housing sections (1, 2) which are pivotable relative to one another, of which a first housing section (1) serves as a handle and accommodates a drive unit (4) for driving a drive shaft (5), and of which a second housing section (2) carries a brush-head (3), which is drivable by the drive shaft, which second housing section (2) is pivotable relative to the drive shaft (5) about a pivot (6), characterized in that the toothbrush comprises a spring device having at least one spring (14) which acts between the second housing section (2) and the drive shaft (5), the second housing section (2) being pivotable relative to the first housing section (1) about the pivot (6) against a pressure exerted by the spring (14) during use of the toothbrush, which spring snaps when a given pressure threshold is exceeded and which pivot is disposed in the second housing section and also forms at least a part of a mechanical coupling between the drive shaft and the second housing section.

2. A toothbrush as claimed in claim 1, characterized in that the second housing section (2) is provided with a coupling member (8) as a part of said mechanical coupling, which coupling member (8) is pivotable about the pivot (6), and the second housing section is detachably coupled to the drive shaft (5) by means of the coupling member.

3. A toothbrush as claimed in claim 2, characterized in that there is provided a second spring (16) having one end fixedly connected to the coupling member (8) and having another end which snaps past a projection (18) of the second housing section (2) when the pressure threshold is reached.

4. A toothbrush as claimed in claim 3, characterized in that the second housing section (2) resumes its original position when the pressure decreases after the threshold has been exceeded.

5. A toothbrush as claimed in claim 1, characterized in that the spring device comprises a plate (12) arranged in the second housing section (2), which plate has an opening (13) through which the drive shaft (5) extends and which plate has resilient arms (14), which are in resilient engagement with the drive shaft, and a stop (15), against which the drive shaft abuts after snapping.

6. A toothbrush as claimed in claim 5, characterized in that the plate (12) is detachably mounted in the second housing section (2).

7. A toothbrush as claimed in claim 5 characterized in that there is provided a second spring (16) having one end fixedly connected to the coupling member (8) and having another end which snaps past a projection (18) of the second housing section (2) when the pressure threshold is reached.

* * * * *